(12) United States Patent
Che et al.

(10) Patent No.: US 7,582,750 B2
(45) Date of Patent: Sep. 1, 2009

(54) METHOD FOR CONVERSION OF TERMINAL ALKENES TO ALDEHYDES USING RUTHENIUM (IV) PORPHYRIN CATALYSTS

(75) Inventors: Chi-Ming Che, Hong Kong (HK); Jian Chen, Shanghai (CN)

(73) Assignee: University of Hong Kong, Hong Kong (CN)

( * ) Notice: Subject to any disclaimer, the term of this patent is extended or adjusted under 35 U.S.C. 154(b) by 796 days.

(21) Appl. No.: 10/920,529

(22) Filed: Aug. 17, 2004

(65) Prior Publication Data

US 2006/0041121 A1 Feb. 23, 2006

(51) Int. Cl.
*C07B 47/00* (2006.01)
(52) U.S. Cl. ...................................... 540/145
(58) Field of Classification Search ................ 540/145
See application file for complete search history.

(56) References Cited

OTHER PUBLICATIONS

J. Smidt et al., "Katalytische Umsetzungen von Olefinen an Platinmetall-Verbindungen," Consortium fur Elektrochemische Industrie GmbH, 1958, University of Hong Kong Libraries.
G. Golubkov et al., "High-Valent Magnanese Corroles and the First Perhalogenated Metallocorrole Catalyst," Angew. Chem. Int. Ed., 2001, 40, No. 11, WILEY-VCH Verlag GmbH.
Z. Gross et al., "Epoxidation Catalysis by a Manganese Corrole and Isolation of an Oxymanganese (v) Corrole," Angew. Chem. Int. Ed., 2000, 39, No. 22, WILEY-VCH Verlag GmbH.
J. Smidt et al., "The Oxidation of Olefins with Palladium Chloride Catalysts," Angew. Chem. Internat. Edit., 1962, vol. 1, No. 2, Munich, Germany.
X. Yu et al., "Polymer-Supported Ruthenium Porphyrins: Versatile and Robust Epoxidation Catalysts with Unusual Selectivity," J. Am. Chem. Soc., 2000, 122, 5337-5342, Amer. Chem.
J. Groves et al., "Rapid Catalytic Oxygenation of Hydrocarbons by Ruthenium Pentafluorophenylporphyrin Complexes," J. Am. Chem. Soc., 1996, 118, 8961-8962, Amer. Chem. Society.
F. Minisci et al., "Kharasch and Metalloporphyrin Catalysis in the Functionalization of Alkanes, Alkenes, and Alkylbenzenes," J. Am. Chem. Soc., 1995, 117, 226-232.
G. Molander and K. Cameron, "Neighboring Group Participation in Lewis Acid-Promoted . . . ," J. Amer. Chem. Soc.., 1993, 115, 830-846, American Chem. Society, Boulder, CO.
J. Kinneary et al., "Mechanistic Studies of Alkene Epoxidation Catalyzed bu Nickel (II) Cyclam Complexes," J. Am. Chem. Soc., 1988, 110, 6124-6129, Amer. Chem. Soc., NY.
J. Collman, "Oxygenation of Styrene by Cytochrome P-450 Model Systems: A Mechanistic Study," J. Am. Chem. Soc., 1986, 108, 2588-2594, Amer. Chem. Society, Standford, CA.
R. Zhang et al., "Highly Efficient Asymmetric Epoxidation of Alkenes with a D4-Symmetric Chiral Dichlororuthenium (IV) Porphyrin Catalyst," J. Org. Chem., 2001, 66, 8145-8153.
C. Liu et al., "Ruthenium meso- Tetrakis(2,6-dichlorophenyl)porphyrin Complex Immobilized in Mesoporous . . . ," J. Org. Chem., 1998, 63, 7364-7369, Hong Kong.

B. Ranu and U. Jana, "Indium(III) Chloride-Promoted Rearrangement of Epoxides: A Selective . . . ," J. Org. Chem., 1998, 8212-8216, Calcutta.
S. Kulasegaram and R. Kulawiec, "Palladium-Catalyzed Isomerization of Aryl-Substituted Epoxides," J. Org. Chem., 1997, 62, 6547-6561, Washington, D.C.
R. Sudha et al., "Chemo- and Regioselective Conversion of Epoxides to Carbonyl Compounds in 5 M Lithium Perchlorate . . . ," J. Org. Chem., 1996, 61, 1877-1879, Madras, India.
G. Molander et al., "A Novel Concept for Regiochemical and Stereochemical Control in Lewis Acid Promoted [3+3] Annulation Reactions," J. Org. Chem., 1991, 2617-19, Boulder, CO.
H. Alper et al., "Molybdenum Hexacarbonyl Catalyzed Rearrangement of Epoxides," J. Org. Chem., 1976, vol. 41, No. 22, 3611-3613, Ottawa, Canada.
Z. Gross and S. Ini, "Asymmetric Catalysis by a Chiral Ruthenium Porphyrin: Epoxidation, Hydroxylation . . . ," Organic Letters, 1999, vol. 1, No. 13, 2077-2080, Israel.
T. Lai et al., "Aerobic Enantioselective Alkene Epoxidation by a Chiral Trans-Dioxo(D4-Porphyrinato)Ruthenium (VI) Complex," Chem. Comm., 1998, 1583-1584, China.
T. Hosokawa, "Palladium(II)-Catalysed Oxidcation of Carbon-Carbon Double Bonds . . . ," J. Chem. Soc., Chem. Commun., 1991, 1559-1560, Osaka, Japan.
T. Wenzel, "Oxidation of Olefins to Aldehydes Using a Palladium-Cooper Catalyst," J. Chem. Soc., Chem. Commun., 1993, 862-864, Union Carbide Corp., South Charleston, WV.
B. Feringa, "Catalytic Oxidation of Alk-1-enes to Aldehydes," J. Chem. Soc., Chem. Commun., 1986, 909-910, Koninklijke/Shell-Laboratorium, Amsterdam, The Netherlands.
K. Suda et al., "Metalloporphyrin-Catalyzed Regioselective Rearrangement of Monoalkyl-substituted Epoxides . . . ," Tetrahedron Letters, 1999, 40, 7243-7246, Elsevier Science Ltd.
K. Okada et al., "Preparation of 3-Methylenesilacyclobutane and its Use in Organic Synthesis," Tetrahedron Letters, 1995, 36, No. 44, 8067-8070, Elsevier Science Ltd.
G. Molander and S. Andrews, "Bis(Trimethylsilyl) Enol Ethers As 1,3-Dianion Equivalents . . . ," Tetrahedron Letters, 1989, vol. 30, No. 18, 2351-2354, Univ. of Colorado.
J. Tsuji, "Synthetic Applications of the Palladium-Catalyzed Oxidation of Olefins to Ketones," Synthesis, 1983, 369-384, Tokyo Institute of Technology, Japan.

(Continued)

*Primary Examiner*—James O. Wilson
*Assistant Examiner*—Paul V. Ward
(74) *Attorney, Agent, or Firm*—Robert D. Katz; Cooper & Dunham LLP

(57) ABSTRACT

Aldehydes were obtained in excellent yields from ruthenium-porphyrin-catalyzed oxidation of various terminal alkenes with 2,6-dichloropyridine N-oxide under mild conditions. The aldehydes generated from these ruthenium-catalyzed alkene oxidation reactions can be used in-situ for olefination reactions with ethyl diazoacetate in the presence of $PPh_3$, leading to one-pot diazoacetate olefination starting from alkenes.

19 Claims, 8 Drawing Sheets

OTHER PUBLICATIONS

H. Ohtake et al., "The Highly Efficient Oxidation of Olefins, Alcohols, Sulfides and Alkanes with Heteroaromatic N-Oxides . . . ," Heterocycles, 1995, vol. 40, No. 2, 867-903.

C. Kruse et al., "New Methods for the Synthesis of 2-Arylpyrroles," Heterocycles, 1987, vol. 26, No. 12, 3141-3151, Duphar Research Laboratories, The Netherlands.

E. Birnbaum et al., "Catalysis of Aerobic Olefin Oxidation by a Ruthenium Perhaloporphyrin Complex," Inorganica Chimica Acta, 1998, 270, 433-439, Elsevier Science.

Z. Gross and S. Ini, "Dual Role of Pyridine N-Oxides in Ruthenium Porphyrin-Catalyzed Asymmetric Epoxidation of Olefins," Inorg. Chem., 1999, 1446-1449, Amer. Chem. Soc.

A. Berkessel and M. Frauenkron, "Catalytic Asymmetric Epoxidation with a Chiral Ruthenium Porphyrin and N-oxides," J. Chem. Soc., Perkin Trans., 1997, 2265-2266, Germany.

F. Martinez et al., "High Valence Vanadium Complex Promoted Selective Rearrangement of Epoxides to Aldehydes or Ketones," J. Chem. Soc., Perkin Trans., 2000, 1749-1751, Spain.

B. Scharbert et al., "Aerobic Epoxidation with a Ruthenium-Porphyrin Catalyst," Journal of Organometallic Chemistry, 1995, 493, 143-147, Elsevier Science S.A., Germany.

J. Zhang et al., "Dendritic Ruthenium Porphyrins: A New Class of Highly Selective . . . ," Chem. Eur. J., 2002, vol. 8, No. 7, 1554-1562, WILEY-VCH Verlag GmbH, Germany.

J. Zhang and C. Che, "Soluble Polymer-Supported Ruthenium Porphyrin Catalysts for Epoxidation . . . ," Organic Letters, 2002, vol. 4, No. 11, 1911-1914, Amer. Chem. Soc., China.

J. Zhang et al., "Chiral Ruthenium Porphyrin Encapsulated in Ordered Mesoporous Molecular . . . ," Chem. Commun., 2002, 2906-2907, The Royal Society of Chemistry.

P. Maux et al., "New Optically Active Ruthenium Porphyrin Catalysts for Asymmetric Epoxidation of Styrenes," J. of Mol. Catalysis, 2003, 95-103, Elsevier B.V.

G. Mirafzal et al., "A New and Efficient Method for the Selective Olefination of Aldehydes . . . ," J. Am. Chem. Soc., 2002, vol. 124, No. 2, 176-177 , Amer. Chem. Soc.

V. Aggarwal et al., "Generation of Phosphoranes Derived from Phosphites. A New Class of Phosphorous . . . ," J. Am. Chem. Soc., 2003, 125, 6034-6035, American Chemical Society.

Y. Chen et al., "Iron(III) and Ruthenium(II) Porphyrin Complex-Catalyzed Selective . . . ," J. Org. Chem., 2003, 68, 3714-3717 , American Chemical Society.

[Ru^IV(tdcpp)Cl_2] (1)

[Ru^IV(tmp)Cl_2] (2)

Oxidation of 3 with various amounts of Cl₂pyNO catalyzed by 1.

| Entry[a] | Cl₂pyNO | Conversion of 3 (%) | Yield (%)[b] | |
|---|---|---|---|---|
| | | | 5 | 4 |
| 1 | 2.0 | 100 | 49 | 51 |
| 2 | 1.03 | 100 | 0 | 99 |
| 3 | 0.9 | 90 | 0 | >99 |

[a]Reaction conditions: 3: 0.1 mmol, 1: 0.5 mol%, CDCl₃: 0.5 mL; 25 °C, open to air.
[b]Determined by ¹H NMR (based on consumed substrate).

Oxidation of 1,3-dienes 6–12 with Cl$_2$pyNO catalyzed by 1

| Entry[a] | Substrate | Temperature (°C) | Time (h) | Product | Yield[b] (%) |
|---|---|---|---|---|---|
| 1 | 6 | 25 | 0.5 | 13 | 83 |
| 2 | 7 | 25 | 1 | 14 | 99 |
| 3 | 8 | 25 | 0.5 | 15 | 88 |
| 4 | 9 | 25 | 0.5 | 16 | 81 |
| 5[c] | 10 | 25 | 0.5 | 17 | 91[d] |
| 6 | 11 | 25 | 0.5 | 18a | 90 |
| 7 | 12 | 60 | 6 | 19 | 99 |

[a]Reaction conditions: diene: 0.1 mmol, Cl$_2$pyNO: 1.03 equiv, 1: 0.5–1.0 mol%, CDCl$_3$: 0.5–1.0 mL; open to air. [b]Determined by GC or $^1$H NMR. [c]Reaction conditions: diene: 0.65 mmol, Cl$_2$pyNO: 1.03 equiv, 1: 1.0 mol%, CHCl$_3$: 10 mL; open to air. [d]Isolated yield.

Oxidation of terminal alkenes 20-26 with Cl₂pyNO catalyzed by 1

R = H: 20, F: 21,
Me: 22, MeO: 24

23   25   26

R = H: 27, F: 28,
Me: 29, MeO: 31

30   32   33

| Entry[a] | Substrate | Temperature (°C) | Time (h) | Product | Yield[b] (%) |
|---|---|---|---|---|---|
| 1 | 20 | 60 | 12 | 27 | 99 |
| 2 | 21 | 60 | 12 | 28 | 99 |
| 3 | 22 | 60 | 2 | 29 | 96 |
| 3 | 22 | 25 | 60 | 29 | 99 |
| 4 | 23 | 25 | 0.5 | 30 | 91 |
| 5 | 24 | 25 | 0.5 | 31 | 99 |
| 6 | 25 | 25 | 0.5 | 32 | 92 |
| 7 | 26 | 60 | 24 | 33 | 0[c] |

[a]Reaction conditions: alkene: 0.1 mmol, Cl₂pyNO: 1.03 equiv, 1: 1.0–2.0 mol%, CDCl₃: 0.5–2.0 mL; open to air. [b]Determined by GC or ¹H NMR. [c]The corresponding epoxide was produced in 99% yield (determined by ¹H NMR).

METHOD FOR CONVERSION OF TERMINAL ALKENES TO ALDEHYDES USING RUTHENIUM (IV) PORPHYRIN CATALYSTS

BACKGROUND OF THE INVENTION

Wacker-type alkene oxidation to carbonyl compounds is one of the most important oxidation reactions in synthetic chemistry and pharmaceutical industry (Smidt et al. *Angew. Chem.* (1959), Vol. 71, page 176; Smidt et al. *Angew. Chem. Int. Ed. Engl.* (1962), Vol 1, page 80; Tsuji, *Synthesis* (1984), page 369; Tsuji, (1998) *Palladium Reagents and Catalysts Innovation in Organic Synthesis*; John Wiley & Sons, New York). Conversion of alkenes $RCH=CH_2$ to acetaldehyde (R=H) or methyl ketones (R≠H) through Wacker process (FIG. 1a) has been well documented by Smidt and Tsuji; however, highly selective formation of aldehydes from catalytic oxidation of $RCH=CH_2$ (R≠H) without C=C bond cleavage (FIG. 1b) remains a challenge. Previous work by Feringa (Feringa, *Chem. Commun.* (1986), page 909), Murahashi (Murahashi et al., *Chem. Commun.*, (1991), page 1559), and Wenzel (Wenzel et al. *Chem. Commun.* (1993), page 862) showed that oxidation of aliphatic alkenes (such as oct-1-ene and dec-1-ene), N-allyl amides/lactams, and allyl esters with $O_2$ or air in the presence of certain palladium or palladium/copper catalysts affords a mixture of aldehyde and methyl ketone products. Recently, Ho and co-workers reported palladium/copper-catalyzed oxidation of a few 1,5-aliphatic dienes with $O_2$ to form aldehydes in 60-99% yields (Ho et al. *Tetrahedron Lett.* (2003), Vol. 44, page 6955).

In efforts to develop new oxidation technology based on ruthenium porphyrin catalysts, we found that the oxidation of a wide variety of terminal alkenes with 2,6-dichloropyridine N-oxide ($Cl_2pyNO$) in the presence of dichlororuthenium (IV) porphyrin catalysts $[Ru^{IV}(por)Cl_2]$ (por=tdcpp 1, tmp 2, where $H_2$tdcpp=meso-tetrkis(2,6-dichlorophenyl)porphyrin and $H_2$tmp=meso-tetramesitylporphyrin) produced aldehydes in up to 99% yields with 100% substrate conversion without C=C bond cleavage. The present invention describes the first ruthenium-catalyzed "Wacker-type oxidation" of terminal alkenes (Hirobe et al., *Heterocycles* (1995), Vol. 40, page 867; Groves et al., *J. Am. Chem. Soc.* (1996), Vol. 118, page 8961; Berkessel et al., *J. Chem. Soc. Perkin Trans.* 1 (1997), page 2265; Che et al., *Chem. Commun.* (1998), page 1583; Che et al., *J. Org. Chem.* (1998), Vol. 63, page 7364; Gross et al. *Org. Lett.* (1999), Vol. 1, page 2077; Gross et al., *Inorg. Chem.* (1999), Vol. 38, page 1446; Che et al., *J. Am. Chem. Soc.* (2000), Vol. 122, page 5337; Che et al., J. Org. Chem. (2001), Vol. 66, page 8145; Che et al., *Chem. Eur. J.* (2002), Vol. 8, page 1554; Che et al., *Org. Lett.* (2002), Vol. 4, page 1911; Che et al., *Chem. Commun.* (2002), page 2906; Berkessel et al., *Chem. Eur. J.* (2003), Vol. 9, page 4746; Simonneaux et al., *J. Mol. Catal. A* (2003), Vol. 206, page 95; Gray et al., *Inorg. Chim. Acta* (1998), Vol. 270, page 433), which apparently proceeded by a different mechanism from those proposed for the palladium- or palladium/copper-catalyzed reactions reported by the respective groups of Feringa, Murahashi, Wenzel and Ho. The realization of a one-pot diazoacetate olefination directly from aldehyde substrates generated in-situ from this ruthenium-porphyrin-catalyzed alkene oxidation reaction is also reported herein.

SUMMARY OF THE INVENTION

The invention provides a mild and practical protocol using $[Ru^{IV}(tdcpp)Cl_2]$ as a catalyst for highly regioselective formation of aldehydes from terminal alkenes without C=C bond cleavage. This protocol is a supplement to the Wacker process for oxidation of terminal alkenes to ketones or aldehydes. The catalytic reactions reported herein can be conducted in air at room temperature, affording a series of isolable β-γ-unsaturated aldehydes in good-to-excellent yields. The present work provides a new, practical, and convenient method for preparing multi functional compounds.

DETAILED DESCRIPTION OF THE INVENTION

The present invention provides a practical and mild process for highly selective conversion of terminal alkenes to aldehydes via a subsequent epoxidation/isomerization route using using non-chiral metalloporphyrin catalysts represented by structural formula:

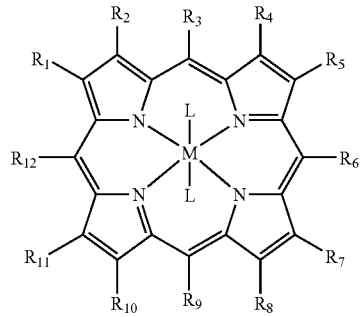

wherein
each $R_1$-$R_{12}$ is independently H, optionally substituted hydroxyl, optionally substituted amino, halogen, —CN, —$NO_2$, optionally substituted $C_{1-20}$ alkyl, optionally substituted phenyl; optionally substituted naphthyl; optionally substituted anthracenyl, —$SR^{13}$, —$SO_2R^{13}$, —$CO_2R^{13}$, and optionally substituted heteroatom-containing aromatic ring, in which the optional substitutents are independently selected from the foregoing alkyl, phenyl, naphthyl, anthracenyl and heteroatom-containing aromatic groups; $R^{13}$ is independently selected from the same groups as $R^1$ other than —$SR^{13}$ and —$SO_2R^{13}$; and L is a halogen molecule, solvent molecule, CO or $R^1$. The various R groups may be optically pure or can be stereo and regio isomers.

Figure 1:
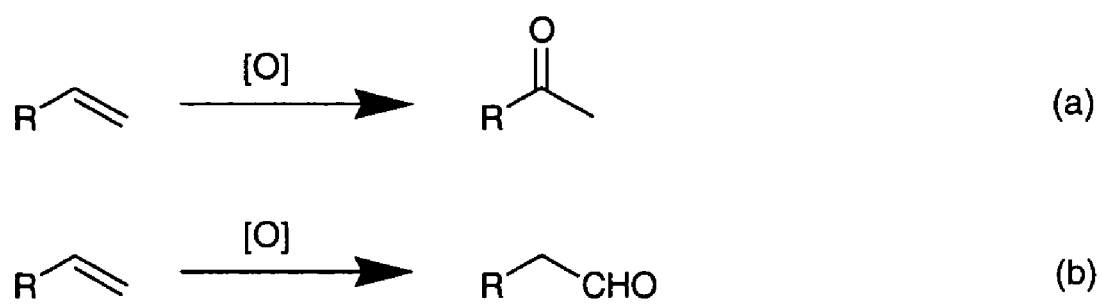
FIG. 1. illustrates the conversion of alkenes $RCH=CH_2$ to acetaldehyde (R=H) or methyl ketones (R≠H) through oxidation process.
Figure 2:
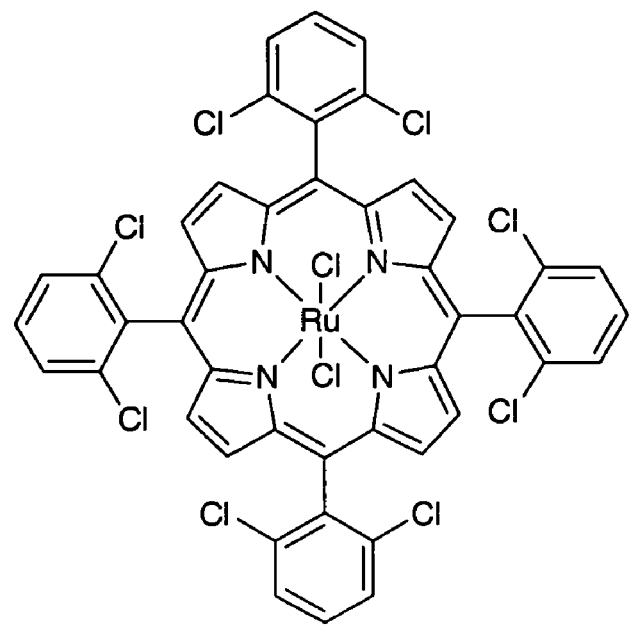
FIG. 2. provides examples of metalloporphyrin catalysts capable of catalyzing the highly selective conversion of terminal alkenes to aldehydes via a subsequent epoxidation/isomerization route.
Figure 2:
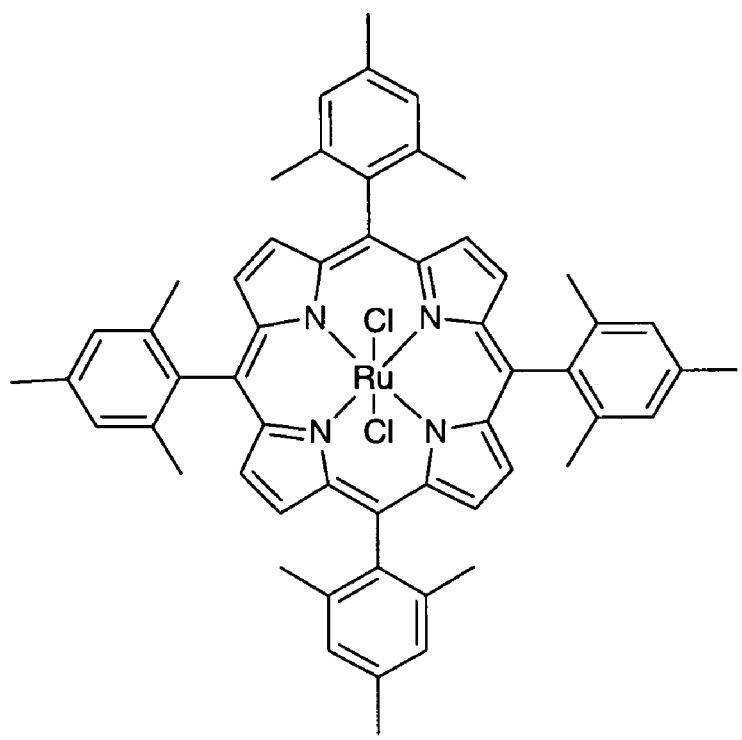
Figure 3:
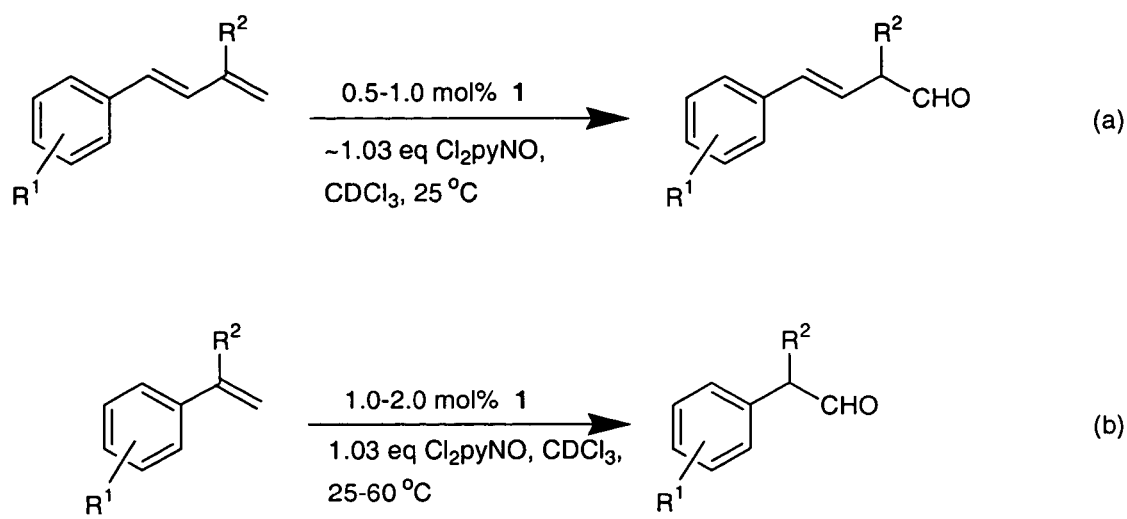
FIG. 3. illustrates the described method which involves the highly selective conversion of terminal alkenes to aldehydes via a subsequent epoxidation/isomerization route using metalloporphyrins as general and efficient catalysts.

In an embodiment of this invention, the metalloporphyrin is a transition metal porphyrin, such as ruthenium, manganese, iron, osmium, copper or cobalt porphyrin. In an embodiment of this invention, the porphyrin ligand is a tetraphenylporphyrin and the phenyl rings are attached at the mesopositions of the porphyrin. In an embodiment of the present invention, the catalysts are capable of exhibiting regioselectivity. Two of the preferred catalysts are shown in FIG. 2. In an embodiment of the present invention, the catalysts are capable of selectively catalyzing oxidation of C═C bonds without C—C bond cleavage. In an embodiment of this invention, the regioselectivity is the oxidation of terminal C═C bonds.

Additionally, the present invention provides a method for the preparation of carbonyl compounds with the catalysts from alkenes as starting materials. Further, the present invention provides a method for producing primary aldehydes with the catalyst. The present invention also provides a method for producing regioselective carbonyl compounds with the catalyst. Preferably, the method involves the use of an oxidant which selectively alters the oxidation state of the substrate, preferably in the presence of a solvent. The solvent can be $CH_3OH$, $CH_3CN$, N,N-dimethylformaldehyde (DMF), $C_4H_4Cl_2$, $CH_2Cl_2$ and benzene. A typical oxidant is $Cl_2pyNO$. In an embodiment of this invention, the substrate is an alkene derivative, or a hydrocarbon containing a C═C functional group. As shown in the figures, carbon to which the alkene moiety is attached can be a part of a cyclic or non-cyclic moiety, which in turn can be substituted with a functional group such as $CO_2Me$ or by an aromatic or cycloaliphatic group.

As used herein, the term "regioselective" refers to selection of terminal C═C bonds over internal C═C bond that undergo reaction. The term "conversion" refers to the relative number of molecules of substrate that is consumed under the applied reaction conditions.

EXAMPLES

Example 1

Regioselective Conversion of Terminal Alkenes to Aldehydes Via a Subsequent Epoxidation/Isomerization Route Catalyzed by Either Dichlororuthenium(IV) Porphyrins 1 or 2

The invention relates to a practical and mild method for the synthesis of aldehydes using either dichlororuthenium(IV) porphyrins 1 or 2 (prepared according to Leung et al. *J. Chem. Soc. Dalton Trans* (1997), page 237) as general and effective catalysts for the oxidation of terminal alkenes.

Typical conditions employ 0.1 mmol of alkene substrate, $Cl_2pyNO$ (1.03 equiv), and 1 (0.5-2.0 mol %) dissolved in $CDCl_3$ (0.5-1.0 mL) in a NMR tube at room temperature or 60° C. The progress of the reaction was monitored by $^1H$ NMR. After determination of the product yield by $^1H$ NMR spectroscopy, the reaction mixture was separated by flash chromatography on silica gel. For the large-scale reaction, 0.65 mmol of alkene substrate, $Cl_2pyNO$ (1.03 equiv), and 1.0 mol % of 1 in 10 mL of $CHCl_3$ were used and reaction was carried out at room temperature for 30 min.

Figure 4:
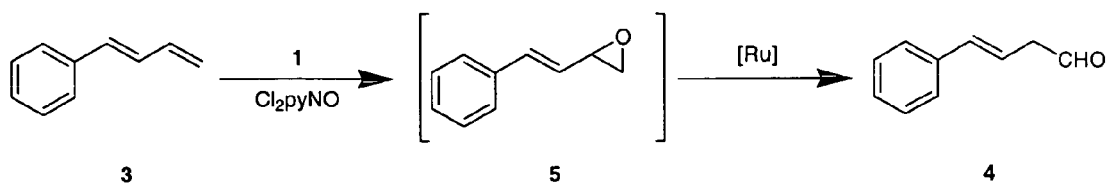
FIG. 4. provides representative examples of oxidation of 1-phenyl-1,3-butadiene (3) with various amounts of $Cl_2pyNO$ catalyzed by a dichlororuthenium(IV) porphyrin to give the corresponding aldehyde (4) or epoxide (5) in good to excellent yields and excellent regioselectivity.

With 0.5 mol % catalyst loading, a solution of 1-phenyl-1,3-butadiene (3) and 1.03 equiv $Cl_2pyNO$, in $CDCl_3$ was stirred for 30 min at room temperature, affording the β-γ-unsaturated aldehyde 4-phenyl-but-3-enal (4, styrylacetaldehyde) in 99% yield (FIG. 4). No ketone products were detected in the reaction mixture. The reaction gave similar results with $CHCl_3$ and $CH_2Cl_2$ as solvents. Other solvents, such as benzene, toluene, acetone, ether, and methanol, were inferior to $CHCl_3$ and $CH_2Cl_2$ for this catalytic process.

The 1,3-diene 3 was first oxidized by $Cl_2pyNO$ to form epoxide 5 in the presence of catalyst 1. The same catalyst, or its derivative, induced subsequent isomerization of the epoxide to β-γ-unsaturated aldehyde (Alper et al. *J. Org. Chem.* (1976), Vol. 41, page 3611; Sankararaman et al. *J. Org. Chem.* (1996), Vol. 61, page 1877; Kulawiec et al. *J. Org. Chem.* (1997), Vol. 62, page 6547; Ranu et al. *J. Org. Chem.* (1998), Vol. 63, page 8212; Suda et al. *Tetrahedron Lett.* (1999), Vol. 40, page 7243; Llama et al. *J. Chem. Soc. Perkin Trans.* 1 (2000), page 1749). We abbreviate the epoxidation of terminal alkenes followed by isomerization of the epoxide products as E-I reactions.

To provide support for the above mechanism, we examined the effect of $Cl_2pyNO$ on the catalysis (FIG. 4). With $Cl_2pyNO$ in excess, the yield of aldehyde 4 significantly decreased from 99% to 51%, and epoxide 5 was obtained in 49% yield. This could be rationalized by the coordination of epoxide to the active ruthenium porphyrin species for the isomerization reactions. Excess $Cl_2pyNO$ would compete with the epoxide for coordination to ruthenium, thus decreasing the aldehyde yield. We found that the use of 1.01-1.03 equiv $Cl_2pyNO$ could give the best results in terms of reaction completion time (30 min) and aldehyde yield (99%). Changing the temperature from room temperature to 10° C. or 40° C. did not appreciably affect the reaction.

The E-I reaction of 3 with $Cl_2pyNO$ could be equally efficiently catalyzed by 2 but less efficiently catalyzed by [$Ru^{VI}(tdcpp)O_2$]. Oxidation of 3 with $Cl_2pyNO$ catalyzed by [$Ru^{VI}(tdcpp)O_2$] under similar conditions to those for catalyst 1 (1.03 equiv $Cl_2pyNO$, 1.7 mol % catalyst loading) afforded 4 in 41% yield within 5 h. However, complex [$Ru^{II}(tdcpp)$(CO)] was a relatively inactive catalyst toward the E-I reaction.

Figure 5:
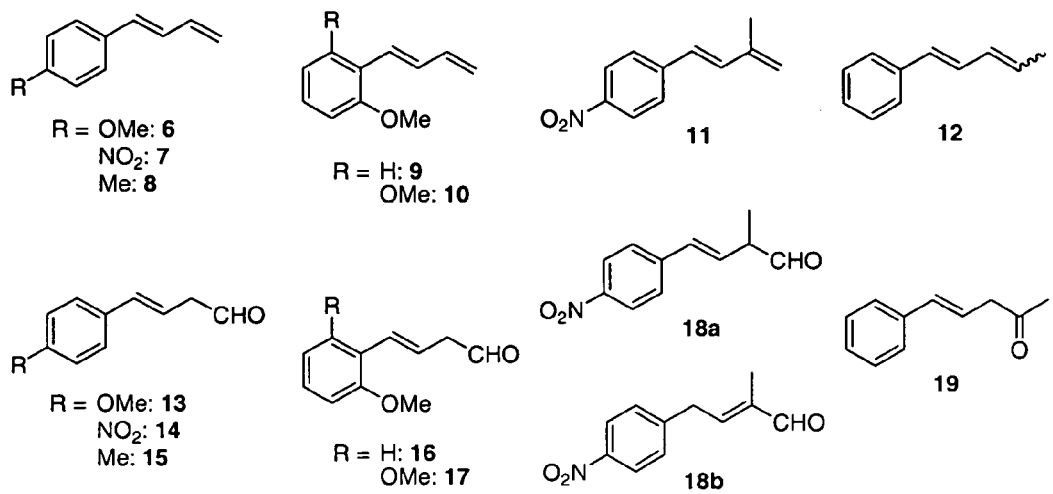
FIG. 5. provides representative examples of conversion of terminal 1,3-dienes using a dichlororuthenium(IV) porphyrin catalyst to give the corresponding aldehydes in good to excellent yields and excellent regioselectivity.

A series of other 1,3-dienes were treated with 1.01-1.03 equiv $Cl_2pyNO$ and 0.5-1.0 mol % 1 at room temperature (FIG. 5). For dienes 6-10, the corresponding β-γ-unsaturated aldehydes 13-17 were obtained in 81-99% yields and were stable enough to be purified by flash chromatography on silica gel. However, the aldehyde product 18a (formed in 90% yield) in the oxidation of diene 11 was converted to 18b upon flash chromatography on silica gel. Non-terminal alkene 12 was oxidized more slowly, affording the β-γ-unsaturated ketone 19 in 99% yield after the reaction proceeded at 60° C. for 6 h.

Figure 6:
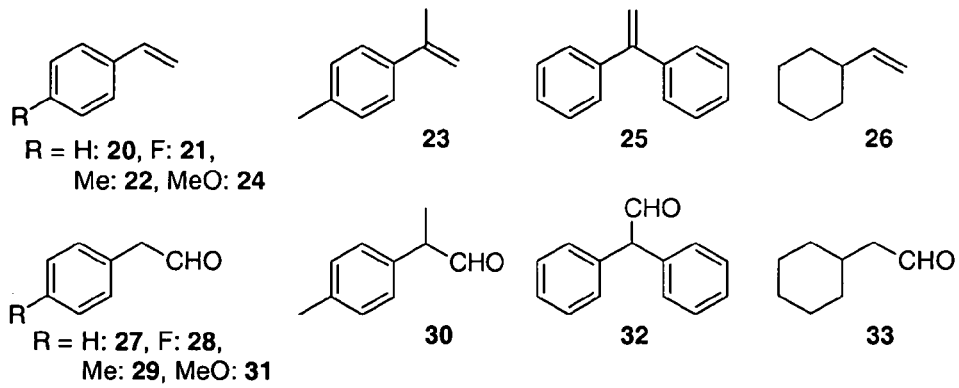
FIG. 6. provides representative examples of conversion of variously substituted alkenes using a dichlororuthenium(IV) porphyrin catalyst to give the corresponding aldehydes in good to excellent yields.

When styrene (20) was treated with 1.03 equiv $Cl_2pyNO$ and 1.0 mol % 1 in refluxing $CH_2Cl_2$ for 5 h, a mixture of styrene oxide and phenylacetaldehyde (27) was obtained in 90% and 10% yield, respectively (Collman et al. *J. Am. Chem. Soc.* (1986), Vol. 108, page 2588; Burrows et al. *J. Am. Chem. Soc.* (1988), Vol. 110, page 6124; Minisci et al. *J. Am. Chem. Soc.* (1995), Vol. 117, page 226; Gross et al. *Angew. Chem. Int. Ed.* (2000), Vol. 39, page 4045; Gray et al. *Angew. Chem. Int. Ed.* (2001), Vol. 40, page 2132). To our surprise, adding more catalyst 1 and allowing the reaction to proceed for a longer time resulted in complete conversion of styrene oxide to aldehyde 27. For example, reaction of styrene with 1.03 equiv $Cl_2pyNO$ in the presence of 2.0 mol % 1 in $CHCl_3$ at 60° C. for 12 h afforded 27 in 99% yield; no benzaldehyde was observed (Gray et al. *Inorg. Chim. Acta* (1998), Vol. 270, page 433). Other styrene derivatives 21-25 could also be converted to the corresponding arylacetaldehydes 28-32 in excellent yields (FIG. 6). However, for the non-aromatic alkene 26, only the epoxide product was obtained.

All the target aldehydes were characterized by $^1H$, $^{13}C$ NMR and IR spectroscopy, and LRMS, HRMS spectrometry. The spectral data of 5 (*Org. Synth., Coll. Vol.* 4, (1963), page. 424), 13 (Frejd et al. *J. Org. Chem.* (1998), Vol. 63, page 3595), 19 (Brookhart et al. *J. Am. Chem. Soc.* (1994), Vol. 116, page 1869) and 27-33 (Palecek et al. *Collect. Czech. Chem. Commun.* (1988), Vol. 53, page 822; Paris et al. *Synth. Commun.* (1991), Vol. 21, page 819; Chikashita et al. *Synth. Commun.* (1987), Vol. 17, page 677; Kulawiec et al. *J. Org. Chem.* (1997), Vol. 62, page 6547; Stratakis et al. *J. Org. Chem.* (2002), Vol. 67, page 8758) are identical with those reported in the literature. 4 $^1H$ NMR (300 MHz, $CDCl_3$): δ9.76 (t, 1H, J=1.8 Hz), 7.23-7.40 (m, 5H), 6.54 (d, 1H, J=16.2 Hz), 6.29 (dt, 1H, J=16.2, 6.9 Hz), 3.36 (ddd, 2H, J=6.9, 1.8, 1.2 Hz); $^{13}C$ NMR (75 MHz, $CDCl_3$): δ199.4, 136.5, 134.9, 128.5, 127.7, 126.2, 119.2, 47.3; IR: 1724, 1599, 1496, 967, 748, 694 $cm^{-1}$; MS (EI) m/z (rel intensity) 146 (31) [M]$^+$; HRMS: calcd for $C_{10}H_{10}O$ 146.0732, found 146.0731. 14 $^1H$ NMR (300 MHz, $CDCl_3$): δ9.57 (d, 1 H, J=7.8 Hz), 8.22 (d, 2H, J=9.0 Hz), 7.38 (d, 2H, J=9.0 Hz), 6.95 (dt, 1H, J=15.3, 6.9 Hz), 6.13 (ddt, 1H, J=15.3, 7.8, 1.5 Hz), 3.78 (d, 2H, J=6.9 Hz), IR: 1689, 1598, 1517, 1347, 980, 856, 736 $cm^{-1}$; MS (EI): m/z 191 (8) [M]$^+$. 15 $^1H$ NMR (300 MHz, $CDCl_3$): δ9.77 (t, 1H, J=1.8 Hz), 7.30 (d, 2H, J=8.1 Hz), 7.15 (d, 2H, J=8.4 Hz), 6.53 (d, 1H, J=15.6 Hz), 6.25 (dt, 1H, J=7.2, 16.5 Hz), 3.34-3.37 (m, 2H); 2.36 (s, 3H); $^{13}C$ NMR (75 MHz, $CDCl_3$): δ199.8, 137.7, 135.1, 133.9, 129.3, 126.2, 118.1, 47.6, 21.3; IR: 1721, 1513, 974, 799, 505 $cm^{-1}$; MS (EI): m/z 160 (27) [M]$^+$; HRMS: calcd for $C_{11}H_{12}O$+H 161.0966, found 161.0959. 16 $^1H$ NMR (300 MHz, $CDCl_3$): δ9.75 (d, 1H, J=2.1 Hz), 7.43 (dd, 1H, J=7.5, 1.5 Hz), 7.23 (td, 1H, J=7.5, 2.1 Hz), 6.83-6.95 (m, 3H), 6.28 (dt, 1H, J=16.2, 7.2 Hz), 3.84 (s, 3H), 3.35 (dt, 2H, J=7.2, 1.5, 2.1 Hz); $^{13}C$ NMR (75 MHz, $CDCl_3$): δ199.7, 156.6, 130.1, 128.8, 126.9, 125.8, 120.7, 119.8, 110.9, 55.5, 48.0; IR: 1721, 1598, 1490, 1245, 1028, 975, 752 $cm^{-1}$; MS (EI): m/z (rel intensity) 176 (6) [M]$^+$; HRMS: calcd for $C_{11}H_2O_2$ 176.0837, found 176.0829. 17 $^1H$ NMR (300 MHz, $CDCl_3$): δ9.68 (t, 1H, J=1.8 Hz), 7.22 (t, 1H, J=8.4 Hz), 6.56 (d, 2H, J=8.4 Hz), 6.50 (d, 1H, J=11.1 Hz), 6.02 (dt, 1H, J=11.1, 7.5 Hz), 3.77 (s, 6H), 3.04 (ddd, 2H, J=7.5, 1.5, 1.5 Hz); $^{13}C$ NMR (75 MHz, $CDCl_3$): δ201.1, 157.6, 129.0, 125.2, 123.5, 113.6, 103.7, 55.6, 44.9; IR: 1724, 1593, 1585, 1471, 1253, 1113, 748 $cm^{-1}$; MS (EI) m/z (rel intensity); 206 (51) [M]$^+$; HRMS: calcd for $C_{12}H_{14}O_3$ 206.0943, found 206.0960. 18b $^1H$ NMR (300 MHz, $CDCl_3$): δ9.47 (s, 1H), 8.20 (d, 2H, J=8.7 Hz), 7.38 (d, 2H, J=9.0 Hz), 6.61 (t, 1H, J=7.2 Hz), 3.82 (d, 2H, J=7.2 Hz), 1.89 (s, 3H); $^{13}C$ NMR (75 MHz, $CDCl_3$): δ194.6, 149.2, 146.9, 145.8, 140.8, 129.4, 124.1, 34.8, 29.7; IR: 1681, 1145, 1606, 1594, 1511, 851, 750, 700 $cm^{-1}$; MS (EI) m/z (rel intensity) 205 (42) [M]$^+$; HRMS: calcd for $C_{11}H_{11}NO_3$+H 206.0817, found 206.0802.

Example 2

Regioselective Conversion of Terminal Alkenes to Aldehydes Via a Subsequent Epoxidation/Isomerization Route Catalyzed by Either Dichlororuthenium(IV) Porphyrins 1 and In-Situ Olefination with Ethyl Diazoacetate in the Presence of $PPh_3$, Leading to One-Pot Diazoacetate Olefination Starting from Alkenes Recently, Woo (Woo et al. *J. Am. Chem. Soc.* (2002), Vol. 124, page 176), Aggarwal (Aggarwal et al. *J. Am. Chem. Soc.* (2003), Vol. 125, page 6034), and Zhang (Zhang et al. *J. Org. Chem.* (2003), Vol. 68, page 3714) reported that iron or ruthenium meso-tetraaryl porphyrins [$Fe^{II}$(ttp)], [$Fe^{III}$(tpp)Cl], or [$Ru^{II}$(tpp)(CO)] can catalyze the olefination of certain classes of aldehydes with ethyl diazoacetate (EDA) in the presence of $PPh_3$. We observed that both 1 and [$Ru^{II}$(tdcpp)(CO)] could also catalyze such olefination reactions. Recognizing that the aldehyde products in the 1-catalyzed E-I reactions could be in-situ used as the substrates for olefination reactions, we were interested in developing a practical one-pot E-I-olefination reaction, i.e. one-pot diazoacetate olefination directly starting from alkenes rather than from aldehydes.

Figure 7:
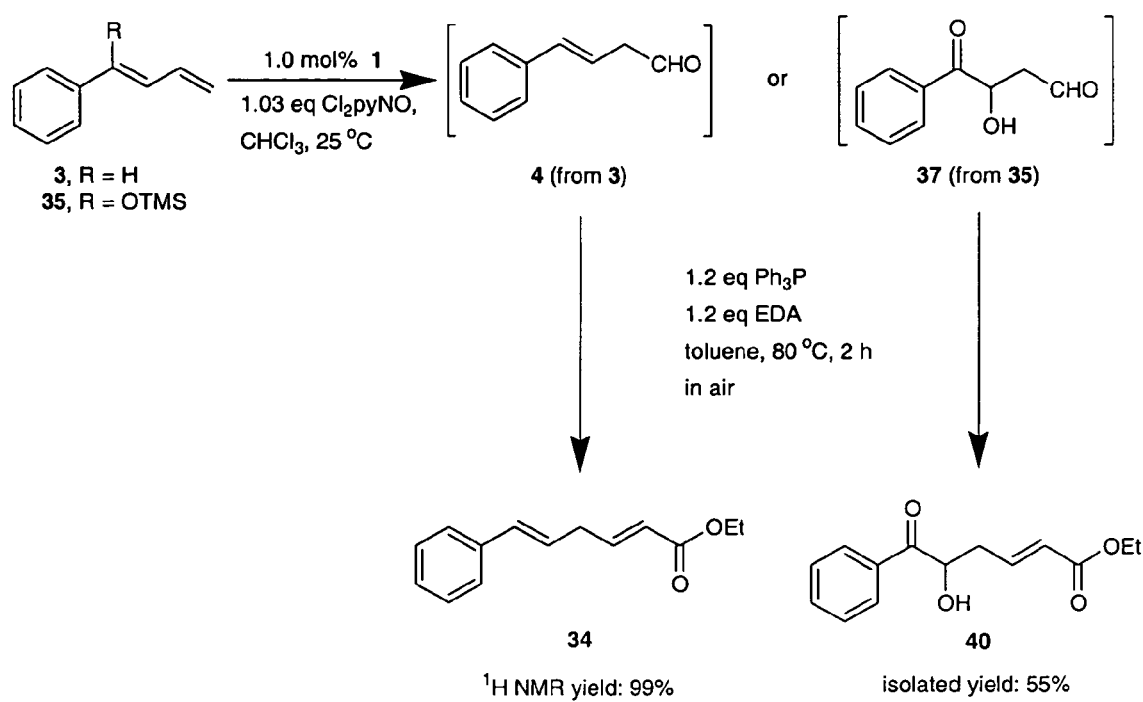
FIG. 7. provides representative examples of conversion of alkenes using a dichlororuthenium(IV) porphyrin catalyst and subsequent in-situ olefination of the aldehyde products obtained with ethyl diazoacetate in the presence of $PPh_3$, leading to one-pot diazoacetate olefination starting from alkenes in good to excellent yields over two steps.

Typical conditions involve using the "1+$Cl_2pyNO$" protocol, 0.1 mmol 3 was converted to aldehyde 4 in $CHCl_3$ within 30 min (the reaction conditions are exactly the same as that stated for EXAMPLE 1). Removal of the solvent, followed by addition of 1.2 equiv $Ph_3P$, 1 mL toluene, and 1.2 equiv EDA, the olefination product 34 was obtained in 99% yield after the reaction mixture was heated at 80° C. for 2 h, cooled to room temperature and separated by flash chromatography on silica gel with petroleum ether/ethyl acetate (3:1) as eluent. Similarly, through a one-pot E-I-olefination reaction of 35, we isolated the olefination product 40 in 55% yield (FIG. 7).

The target olefination products were characterized by $^1H$, $^{13}C$ NMR and IR spectroscopy, and LRMS, HRMS spectrometry. 34 $^1H$ NMR (300 MHz, $CDCl_3$): δ7.22-7.37 (m, 5H), 7.04 (dt, 1H, J=15.3, 6.3 Hz), 6.45 (d, 1H, J=16.2 Hz), 6.19 (dt, 1H, J=15.9, 6.9 Hz), 5.90 (td, 1H, J=1.5, 15.3 Hz), 4.20 (q, 2H, J=6.9 Hz), 3.08-3.13 (m, 2H), 1.29 (t, 3H, J=6.9 Hz); IR: 1720, 1653, 1267, 1160, 1043, 967, 745, 693 $cm^{-1}$; MS (EI) m/z (rel intensity) 216 (67) [M]$^+$. 40 $^1H$ NMR (300 MHz, $CDCl_3$): δ7.91 (d, 2H, J=7.8 Hz), 7.66 (t, 1H, J=7.5 Hz), 7.53 (t, 2H, J=7.5 Hz), 6.94 (dt, 1H, J=7.8, 15.9 Hz), 5.83 (d, 1H, J=15.9 Hz), 5.19-5.15 (m, 1H), 4.18 (q, 2H, J=6.9 Hz), 3.84 (d, 1H, J=6.6 Hz), 2.76-2.84 (m, 1H), 2.41-2.51 (m, 1H), 1.28 (t, 3H, J=6.9 Hz); $^{13}C$ NMR (75 MHz, $CDCl_3$): δ200.5, 165.9, 142.6, 134.4, 133.2, 129.1, 128.6, 124.6, 71.9, 60.4, 38.5, 14.3; IR: 3467, 1716, 1684, 1657, 1598, 1581, 1450, 1271, 1167, 979, 695 $cm^{-1}$; MS (EI) m/z (rel intensity) 248 (0.1) [M]$^+$; HRMS ([M+Na]$^+$): calcd for $C_{14}H_{16}O_4Na$ 271.0941, found 271.0919.

Example 3

Preparation of Synthetically Organic Compounds by Application of the Dichlororuthenium(IV) Porphyrin Catalyzed Oxidation of Silyl Enol Ethers 4-Oxoarylbutanal derivatives are useful compounds for organic synthesis. For example, the preparation and application of 4-oxo-4-phenylbutanal (39) have been extensively studied in the literature. (Kruse et al. *Heterocycles* (1987), Vol. 26, page 3141; Molander et al. *Tetrahedron Lett.* 1989, Vol. 30, page 2351; Molander et al. *J. Org. Chem.* (1991), Vol. 56, page 2617; Molander et al. *J. Am. Chem. Soc.* 1993, Vol.

Figure 8:
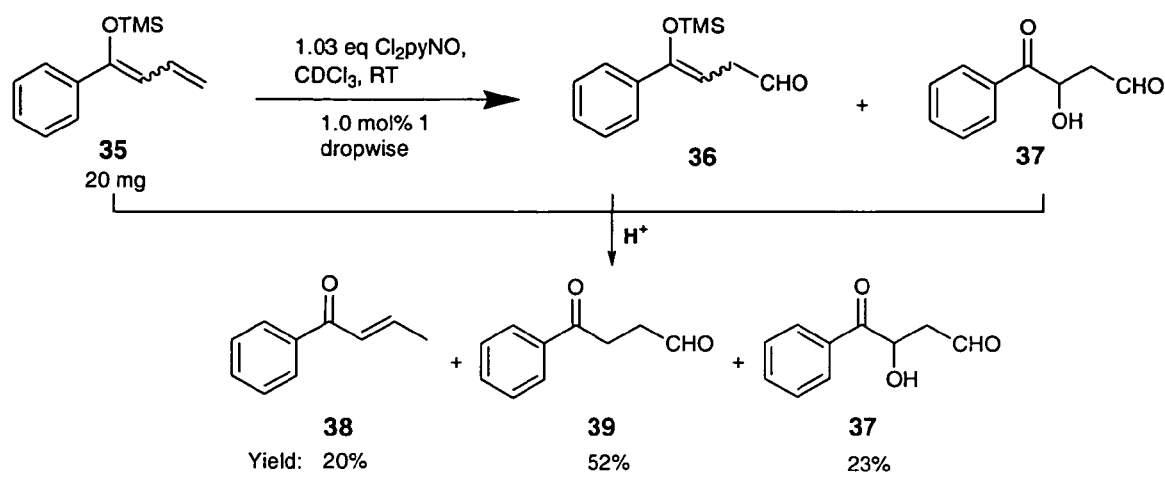
FIG. 8. illustrates the utility of the metalloporphyrin catalyzed oxidation reaction for organic synthesis through the preparation of representative examples of synthetically useful compounds afforded from dichlororuthenium(IV) porphyrin catalyzed oxidative epoxidation/isomerization reaction of silyl enol ethers.

115, page 830; Savoia et al. *Tetrahedron Lett.* (1994), Vol. 35, page 2775; Utimoto et al. *Tetrahedron Lett.* (1995), Vol. 36, page 8067). In this work, we found that 39 could be prepared in 52% NMR yield (isolated yield: 41%) from the E-I reaction of silyl enol ether 35 (FIG. 8). The same reaction also afforded hydroxyl ketoaldehyde 37 in 23% yield. When 2.06 equiv Cl$_2$pyNO were used, 37 could be obtained in 88% yield (determined by $^1$H NMR).

Typical conditions involve dropwise addition of a solution of 1 (0.02 mmol) in CHCl$_3$ (50 mL) over 30 min to a well-stirred solution of 35 (2.0 mmol) and Cl$_2$pyNO (2.2 mmol) in CHCl$_3$ (100 mL) in a 25-mL flask. A drop of 12 N HCl was then added. The resulting mixture was stirred for 5 min. The product was purified by flash chromatography on silica gel.

The spectral data of 38 (Chong et al. *Tetrahedron* 1999, Vol. 55, page 14233) and 39 (Molander et al. *J. Am. Chem. Soc.* 1993, Vol. 115, page 830) are identical with those reported in the literature.

What is claimed is:

1. A method for producing an aldehyde from an unsaturated compound having one or more C═C functional groups, which comprises reacting a pyridine-N-oxide with the unsaturated compound in the presence of a catalytic amount of a ruthenium (IV) porphyrin complex catalyst, wherein the ruthenium (IV) porphyrin complex has the following structure:

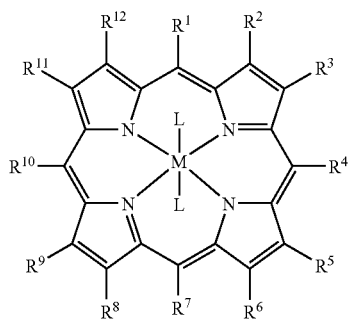

wherein M is a ruthenium (IV) porphyrin complex;
wherein each $R_1$-$R_{12}$ is independently H, optionally substituted hydroxyl, optionally substituted amino, halogen, —CN, —NO$_2$, optionally substituted C$_{1-20}$ alkyl, optionally substituted phenyl; optionally substituted napthyl; optionally substituted anthracenyl, —SR$^{13}$, —SO$_2$R$^{13}$, —CO$_2$R$^{13}$, and optionally substituted heteroatom-containing aromatic ring, in which the optional substituents are independently selected from the foregoing alkyl, phenyl, napthyl, anthracenyl and heteroatom-containing aromatic groups; R$^{13}$ is independently selected from the same groups as R$^1$ other than —SR$^{13}$ and —SO$_2$R$^{13}$; and wherein L is a halogen molecule, solvent molecule, CO or R$^1$.

2. The method according to claim 1, wherein the unsaturated compound comprises a terminal alkene.

3. The method according to claim 1, wherein the pyridine N-oxide comprises 2,6-dichloropyridine N-oxide (Cl$_2$pyNO).

4. The method according to claim 1, wherein the reaction is carried out using CDCl$_3$, CHCl$_3$, CH$_2$Cl$_2$, diethyl ether, acetone, CH$_3$OH, toluene or benzene as a solvent.

5. The method of claim 3, wherein the method is carried out using CDCl$_3$, CHCl$_3$ or CH$_2$Cl2.

6. The method of claim 5, wherein the ruthenium (IV) porphyrin complex exhibits regioselecuvity and provides yields of at least 52 percent.

7. The method according to claim 1, wherein the transition metal porphyrin complex has the structure A or B:

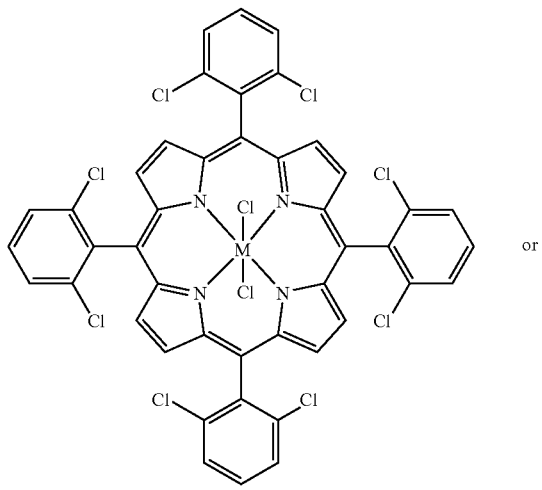

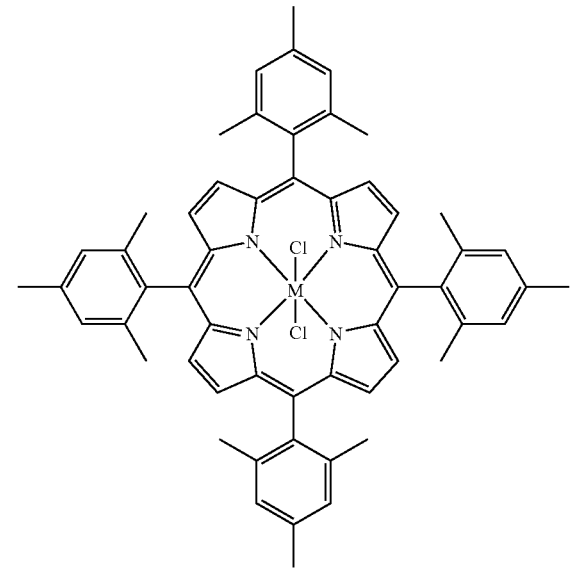

wherein M is ruthenium.

8. The method according to claim 7, wherein the ruthenium (IV) porphyrin complex has structure A or B:

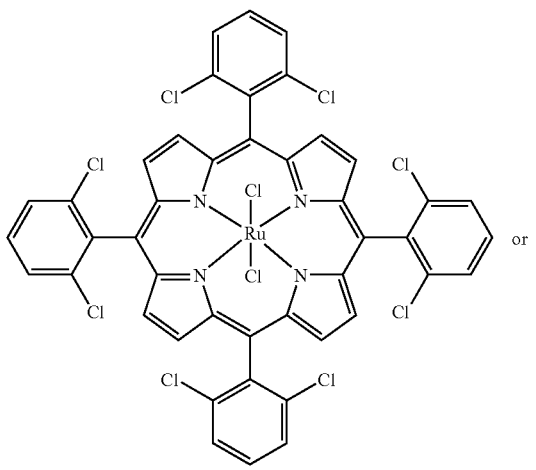

-continued

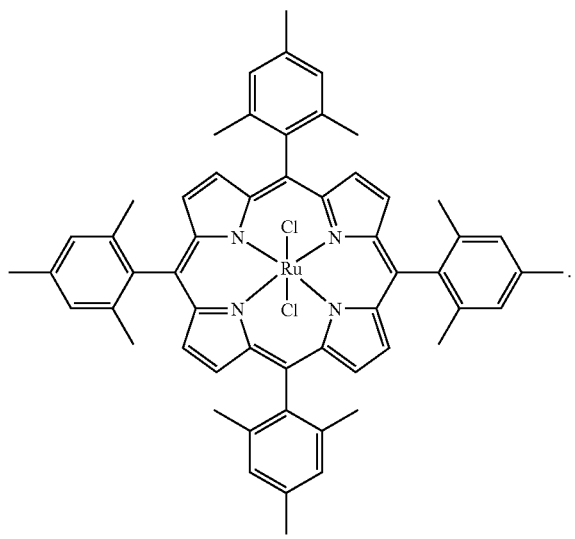

9. A method for producing diazoacetate olefination from an unsaturated compound having one or more C=C functional groups, which comprises catalyzing the reaction of an oxidant with the unsaturated compound in the presence of a catalytic amount of a ruthenium (IV) porphyrin complex and adding a Lewis base and a diazo compound to the reaction, thereby producing an α, β-unsaturated ester of the diazoacetate olefination, wherein the ruthenium (IV) porphyrin complex has the following structure:

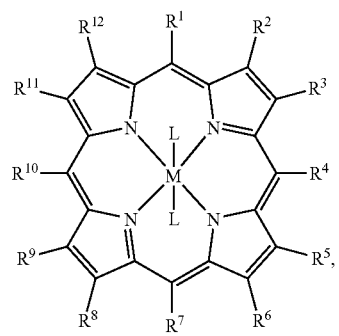

wherein each $R_1$-$R_{12}$ is independently H, optionally substituted hydroxyl, optionally substituted amino, halogen, —CN, —NO$_2$, optionally substituted $C_{1-20}$ alkyl, optionally substituted phenyl; optionally substituted napthyl; optionally substituted anthracenyl, —SR$^{13}$, —SO$_2$R$^{13}$, —CO$_2$R$^{13}$, and optionally substituted heteroatom-containing aromatic ring, in which the optional substituents are independently selected from the foregoing alkyl, phenyl, napthyl, anthracenyl and heteroatom-containing aromatic groups; R$^{13}$ is independently selected from the same groups as R$^1$ other than —SR$^{13}$ and —SO$_2$R$^{13}$;

wherein M is ruthenium; and
wherein L is a halogen molecule, solvent molecule, CO or R$^1$.

10. The method according to claim 9, wherein the unsaturated compound comprises a terminal alkene.

11. The method according to claim 9, wherein the oxidant comprises 2,6-dichloropyridine N-oxide (Cl$_2$pyNO).

12. The method according to claim 9, wherein the Lewis base comprises PPh$_3$.

13. The method according to claim 9, wherein the diazo compound comprises ethyl diazoacetate (EDA).

14. The method according to claim 9, wherein the reaction in carried out with CDCl$_3$, CHCl$_3$, CH$_2$Cl$_2$, diethyl ether, acetone, CH$_3$OH, toluene or benzene as a solvent.

15. The method of claim 11, wherein the Lewis base is PPh$_3$, the diazo compound is ethyl diazoacetate, and the reaction is carried out using CDCl$_3$, CHCl$_3$, CH$_2$Cl$_2$, diethyl ether, acetone, CH$_3$OH, toluene or benzene as a solvent.

16. The method according to claim 9, wherein the ruthenium (IV) porphyrin complex has the structure A or B:

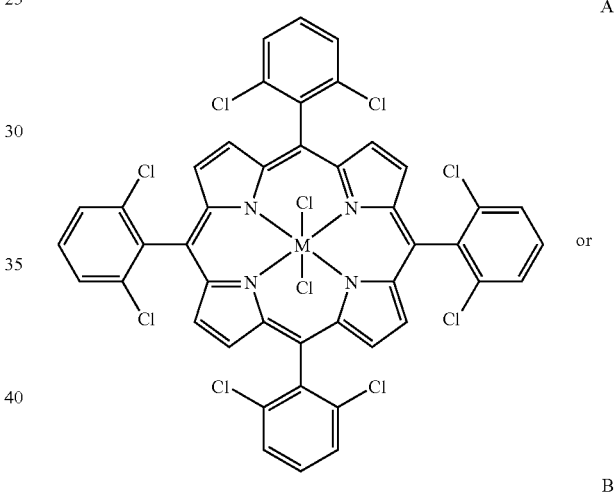

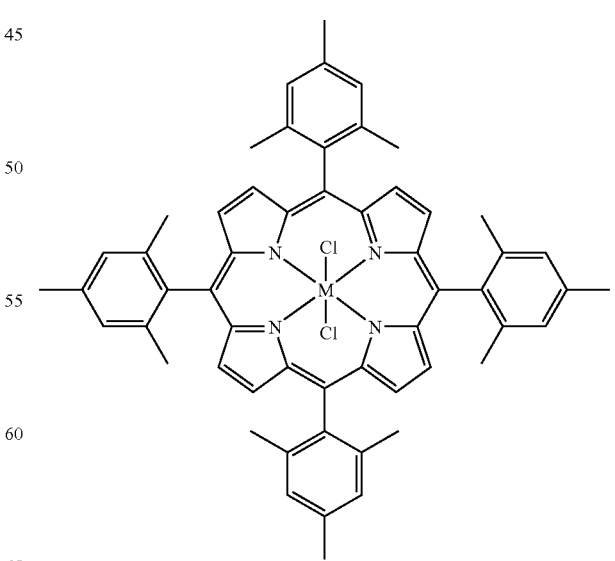

wherein M is ruthenium.

17. The method according to claim 9, wherein the catalyst is a compound having the structure A or B:
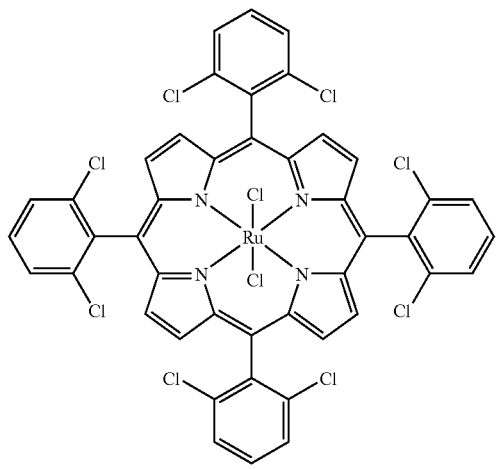
A
or
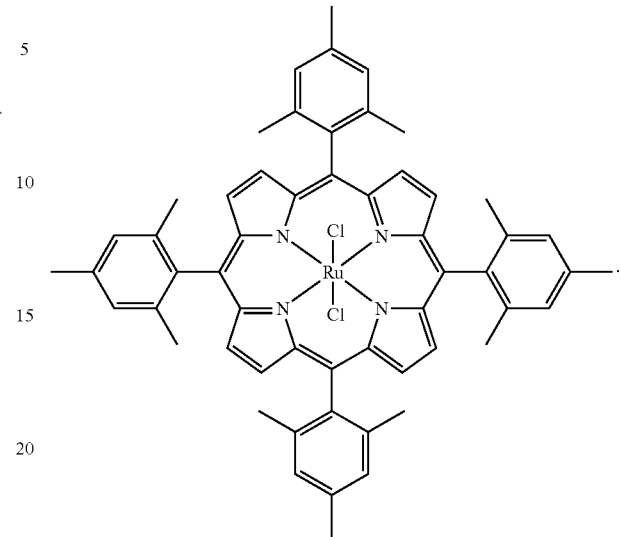
B
18. The method of claim 15 wherein the ruthenium (IV) porphyrin complex exhibits regioselectivity.
19. The method of claim 18, wherein the catalyst exhibits trans-selectivity and yields a trans-α, β-unsaturated ester.
* * * * *